(12) United States Patent
Kuhn et al.

(10) Patent No.: US 11,135,064 B2
(45) Date of Patent: Oct. 5, 2021

(54) IMPLANTS AND METHODS OF USE THEREOF

(71) Applicant: Stryker European Operations Holdings LLC, Kalamazoo, MI (US)

(72) Inventors: Sven Martin Kuhn, Emmendingen (DE); Stefan Gutzeit, Freiburg (DE); Greg Swords, Atlanta, GA (US); Levi Ruthardt, Freiburg (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 170 days.

(21) Appl. No.: 16/128,651

(22) Filed: Sep. 12, 2018

(65) Prior Publication Data
US 2019/0076255 A1    Mar. 14, 2019

Related U.S. Application Data

(60) Provisional application No. 62/557,296, filed on Sep. 12, 2017.

(51) Int. Cl.
| | | |
|---|---|---|
| *A61F 2/28* | (2006.01) | |
| *A61F 2/46* | (2006.01) | |
| *A61F 2/30* | (2006.01) | |

(52) U.S. Cl.
CPC ........ *A61F 2/2875* (2013.01); *A61F 2/30771* (2013.01); *A61F 2/4601* (2013.01);
(Continued)

(58) Field of Classification Search
CPC .. A61F 2/186; A61F 2/82; A61F 2/958; A61F 11/002; A61F 11/00; A61F 11/008;
(Continued)

(56) References Cited

U.S. PATENT DOCUMENTS

| | | | |
|---|---|---|---|
| 3,874,388 A | | 4/1975 | King et al. |
| 6,120,484 A | * | 9/2000 | Silverstein .............. A61F 11/00 424/427 |

(Continued)

FOREIGN PATENT DOCUMENTS

| | | |
|---|---|---|
| DE | 2514142 A1 | 10/1976 |
| DE | 102009036817 A1 | 2/2011 |

OTHER PUBLICATIONS

Jho H.D., Alfieri, A., Endoscopic Endonasal Pituitary Surgery: Evolution of Surgical Technique and Equipment in 150 Operations, Minimally Invasive Neurosurgery, Mar. 2001, pp. 1-12, vol. 44 No. 1, Georg Thieme Verlag Stuttgart, New York.

(Continued)

*Primary Examiner* — Jason-Dennis N Stewart
(74) *Attorney, Agent, or Firm* — Lerner, David, Littenberg, Krumholz & Mentlik, LLP

(57) ABSTRACT

An implant to fill a hole in tissue, such as bone tissue, comprising a first portion that is insertable through the hole when in a first compressed position, wherein the first portion cannot pass through the hole when in a first deployed position; and a second portion that cannot pass through the hole when in the second deployed position. The first and second portions of the implant can be deployed independently. Therefore, in operation, it is possible to insert the first portion of the implant through the hole when in the first compressed position, deploying the first portion to transition it to the first deployed position while the second portion remains in the second compressed position, and then deploying the second portion to transition it to the second deployed position. The devices and methods may be used, for example, in transsphenoidal or other orthopedic surgeries involving bone tissue.

18 Claims, 11 Drawing Sheets

(52) U.S. Cl.
CPC .............. *A61F 2002/2839* (2013.01); *A61F 2002/2885* (2013.01); *A61F 2002/30062* (2013.01); *A61F 2002/3092* (2013.01); *A61F 2002/3093* (2013.01); *A61F 2002/30448* (2013.01); *A61F 2002/30589* (2013.01)

(58) Field of Classification Search
CPC ..... A61F 2/4601; A61F 2/2875; A61M 31/00; A61M 25/00
See application file for complete search history.

(56) References Cited

U.S. PATENT DOCUMENTS

| | | |
|---|---|---|
| 8,740,839 B2 | 6/2014 | Eaton et al. |
| 2008/0015540 A1 | 1/2008 | Muni et al. |
| 2009/0192490 A1 | 7/2009 | Eaton et al. |
| 2010/0106255 A1 | 4/2010 | Dubin |
| 2010/0291401 A1* | 11/2010 | Medina .................. B23K 26/38 428/593 |
| 2014/0172014 A1 | 6/2014 | Fitzgerald et al. |
| 2015/0094642 A1 | 4/2015 | Kesten et al. |
| 2015/0173894 A1 | 6/2015 | Gross et al. |
| 2019/0060125 A1* | 2/2019 | Ngo-Chu .............. A61F 11/002 |

OTHER PUBLICATIONS

Kassam, et al., Endoscopic endonasal skull base surgery: analysis of complications in the authors' initial 800 patients Journal of Neurosurgery, Jun. 2011, pp. 1544-1568, vol. 114, No. 6.

MEDPOR Neuro Implant Product Info by Stryker, retrieved May 15, 2017.

\* cited by examiner

IMPLANTS AND METHODS OF USE THEREOF

CROSS-REFERENCE TO RELATED APPLICATIONS

The present application claims the benefit of the filing of U.S. Provisional Patent Application No. 62/557,296, filed Sep. 12, 2017, the disclosure of which is hereby incorporated herein by reference.

BACKGROUND OF THE INVENTION

The present disclosure generally relates to implants that can be used to fill a hole created in tissue (e.g., bone tissue), as well as methods of use thereof. In particular, the present disclosure includes a detailed description of devices and methods for use during transsphenoidal surgery, which may be necessary to remove a tumor in or near a pituitary gland of a patient. However, it may be understood from the present disclosure that similar, if not the same, devices and methods could be used during many surgeries, such as those in which a hole is created in other body tissue that needs to be filled.

Referring to FIG. 1, the pituitary gland 1 is located in the sellar region at the base of the skull and is protected by dura matter 2 and sphenoid bone 4. Specifically, pituitary gland 1 sits within the sella turcica 3 (reference numeral points to an oval highlighting an area including the sella turica), which is a saddle shaped depression formed within the sphenoid bone 4.

During transsphenoidal surgery, a surgeon will commonly utilize several instruments, including inserting a cutting instrument in a distal direction through the nostrils of the patient into the sphenoid sinus 5 and through the mucosal membrane 8. Then, the surgeon may use the cutting instrument to create a hole in the floor 33 of the sella turcica 3, thereby exposing dura matter 2. Finally, the surgeon may cut through dura matter 2 in order to expose and remove the tumor.

This foregoing approach is widely used in order to gain access to the sellar region because it is relatively minimally invasive. Once the tumor is removed, the surgeon may optionally use a fat graft to fill the empty space in the sellar region where the tumor had been. Then, a surgeon may use a bone implant, a bone graft, a fat graft, fascia lata, fibrin glue, and/or other soft tissue in order to seal or close the hole in the floor 33 of the sella turcica 3. To do so, the surgeon may insert the bone implant through the patient's nostrils along the above-described travel path as the cutting instrument. Then, the surgeon may advance the bone implant through the hole created in the floor 33 of the sella turcica 3 and fix the bone implant in a desired position to fill the hole.

It is important to create a tight closure of the sella turcia with the implant to minimize the risk of infection for the patient. Further, the surgeon will want to minimize the leakage of cerebrospinal fluid ("CSF") from the brain into the sphenoid sinus 5 and nasal cavity. Thus, in many applications, surgeons will use bone implants made of super elastic materials such as silicone to create a tight seal between the bone implant and the hole. However, it can be extremely time consuming for the surgeon to shape and/or arrange these materials so that the bone implant is properly fixed within the hole in the bone. Additionally, some of these bone implants still show high CSF leakage rates and require additional corrective surgery.

In view of the above, there is a need for implants that are safe, simple and easy to use for transsphenoidal applications, as well as other applications, and that provide a tight seal when utilized, for instance, in a defect in the sella turcia.

BRIEF SUMMARY OF THE INVENTION

A first aspect of the present invention is an implant to fill a hole in tissue, such as bone tissue, comprising a first portion having a first compressed position and a first deployed position, wherein the first portion is insertable through the hole when in the first compressed position, and the first portion cannot pass through the hole when in the first deployed position; and a second portion having a second compressed position and a second deployed position, wherein the second portion cannot pass through the hole without deformation when in the second deployed position; and wherein the first and second portions can be deployed independently. The implant may also include an intermediate foam layer to promote tissue ingrowth disposed between the first and second portions, and the intermediate foam layer may comprise an open cell foam. The intermediate foam layer and the first and second portions may be at least partially resorbable. The intermediate foam layer may also have first and second surfaces contacting the first and second portions respectively, wherein the surfaces include an adhesive coating. The first and second portions may also comprise an adhesive coating on at least one surface.

The first portion of the implant may comprise a first sealant layer to create a liquid barrier and a first foam layer to promote tissue ingrowth. The first foam layer may comprise an open cell foam. The second portion of the implant may comprise a second sealant layer to create a liquid barrier and a second foam layer to promote tissue ingrowth. The second foam layer may also comprise an open cell foam. The first and second portions of the implant may also be self-expanding upon deployment in order to transition from their compressed positions to their deployed positions. The first and second portions of the implant may also be inflatable to transition from their compressed positions to their deployed positions. The first and second portions may also be made of a biodegradable material. The first and second portions may also fit within a bore in a cartridge when in their compressed positions. The bore can have any diameter, for instance, between 4 mm and 8 mm.

In one embodiment, the tissue may be the sphenoid bone and the hole may be the sella turcica. The first portion of the implant may contact an inner surface of the bone that surrounds the hole when in the first deployed position. The second portion of the implant may contact an outer surface of the bone that surrounds the hole when in the second deployed position.

A second aspect of the present invention is a tool to deploy an implant to fill a hole in tissue, such as bone tissue, comprising a shaft having first and second ends spaced apart along an axis, wherein the first end is in contact with the implant; a plunger disposed within the shaft adapted to deploy the implant, wherein the plunger can translate within the shaft along the axis in a first direction toward the first end to reach a first stop position such that a first portion of the implant transitions from a first compressed position to a first deployed position while a second portion of the implant remains in a second compressed position, and wherein the first portion is insertable through the hole when in the first compressed position, and the first portion cannot pass through the hole without deformation when in the first deployed position, and wherein the plunger can continue to translate within the shaft along the axis in the first direction to reach a second stop position such that the second portion of the implant transitions from the second compressed position to a second deployed position, and wherein the second portion cannot pass through the hole when in the second deployed position.

A third aspect of the present invention is a method of deploying an implant to fill a hole in tissue, such as bone tissue, comprising inserting a first portion of the implant through the hole, the first portion being in a first compressed position; deploying the first portion of the implant to transition the first portion from the first compressed position to a first deployed position while a second portion of the implant remains in a second compressed position, wherein the first portion cannot pass through the hole when in the first deployed position; and deploying the second portion of the implant to transition the second portion from the second compressed position to a second deployed position, wherein the second portion cannot pass through the hole when in the second deployed position. The method may also be used when the first portion contacts an inner surface of the tissue that surrounds the hole when in the first deployed position and wherein the second portion contacts an outer surface of the tissue that surrounds the hole when in the second deployed position.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

As used herein, the terms "proximal" and "distal," when used in reference to a delivery device, are to be taken as relative to a user of the delivery device. "Proximal" is to be understood as closer to the user and "distal" is to be understood as farther away from the user.

Figure 4:
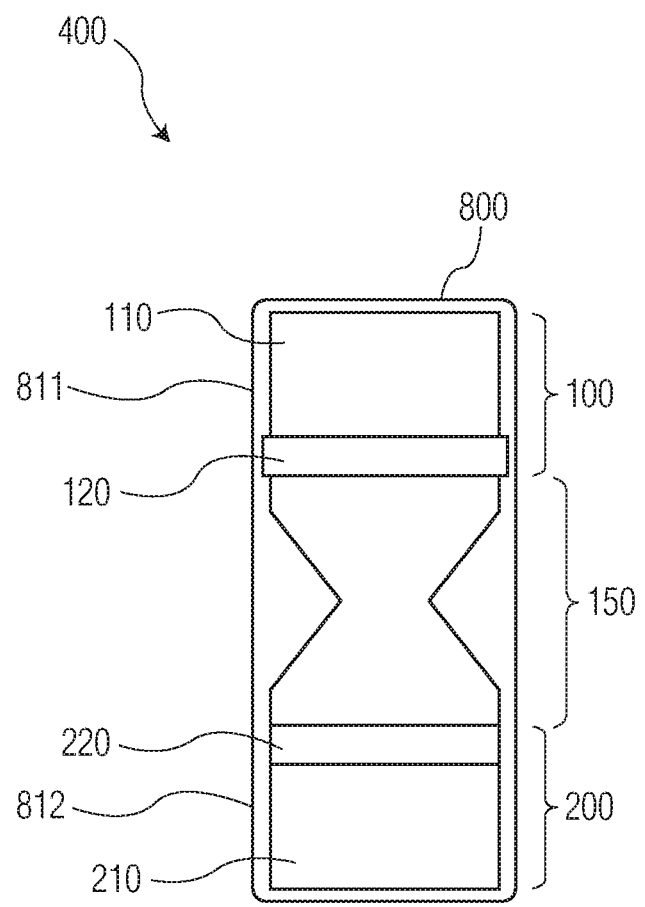
FIG. 4 is a side view of a cartridge and an implant according to one embodiment of the present invention in a compressed position, with the cartridge shown in cross-section.
Figure 5:
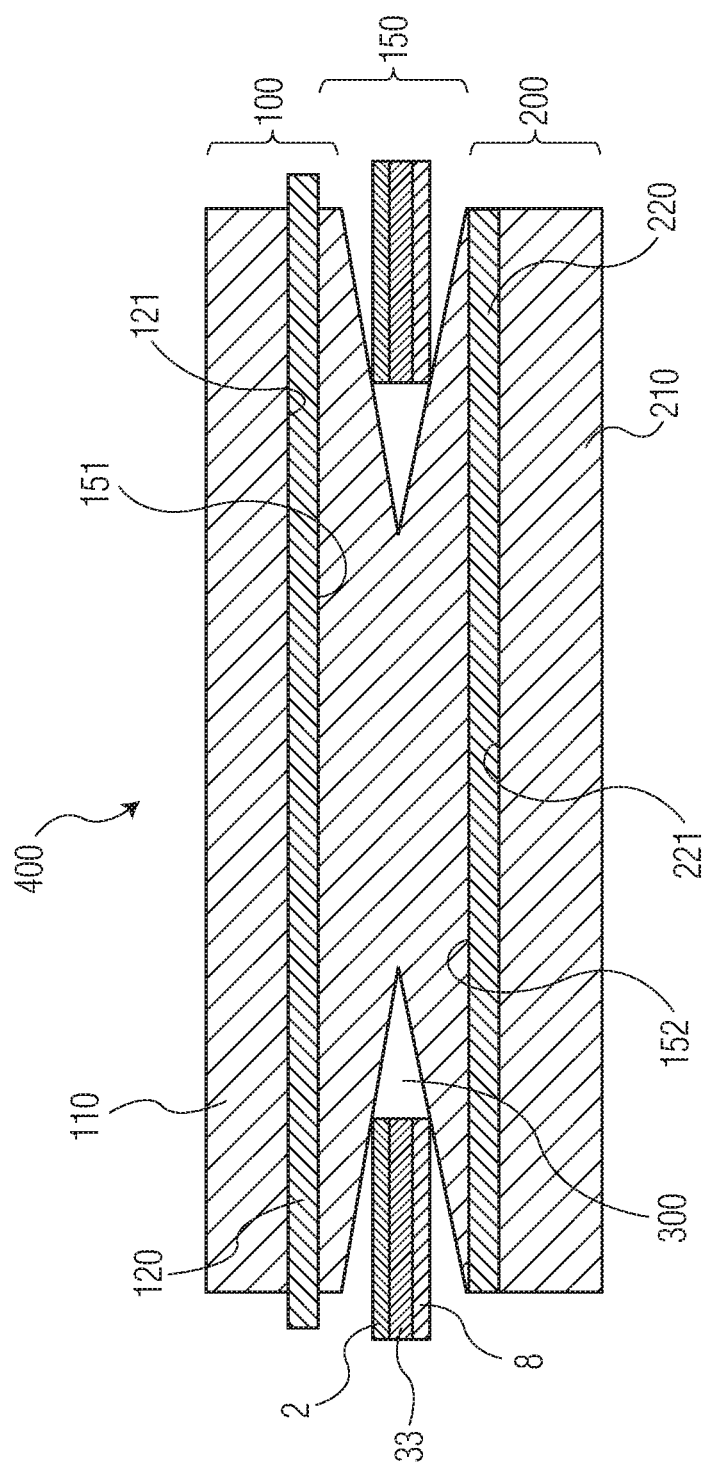
FIG. 5 is a cross-sectional view of the implant of FIG. 4 in a deployed position.
Figure 6:
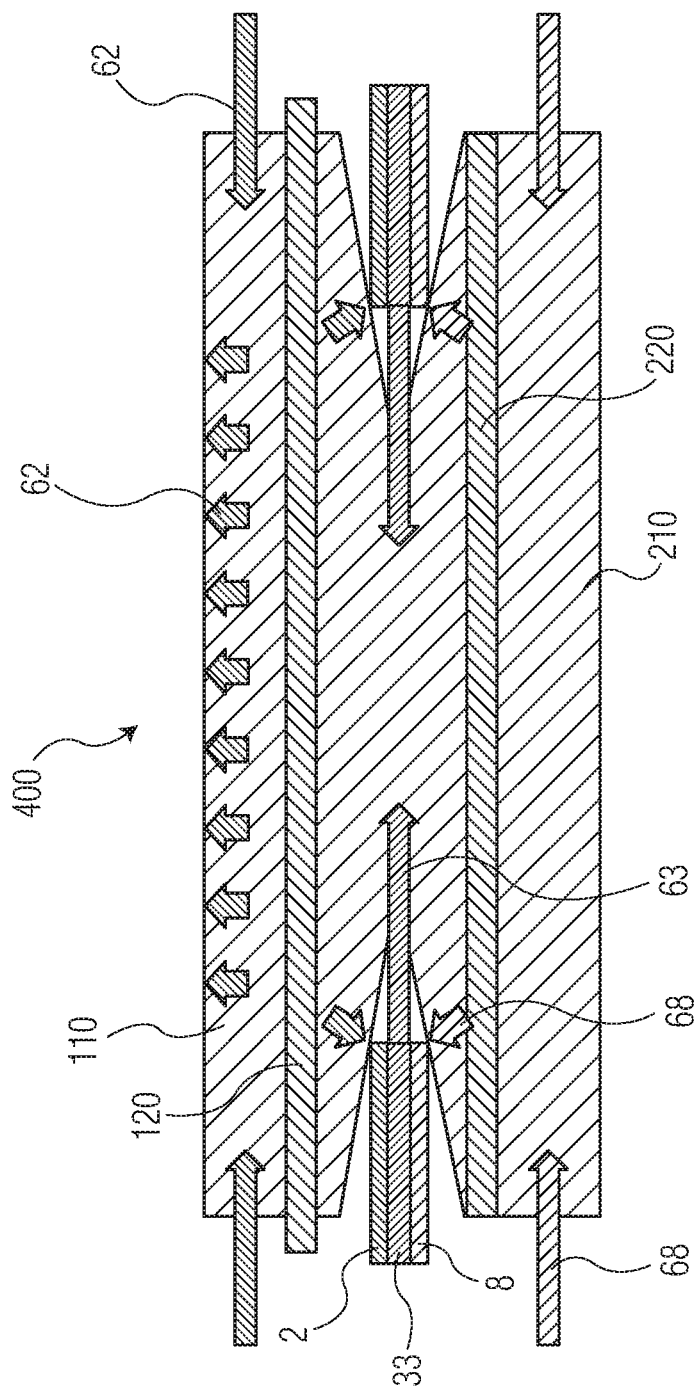
FIG. 6 is a cross-sectional view of the implant of FIG. 5 depicting certain biological interactions.

Referring to FIGS. 4-6, there is shown a bone implant 400 in accordance with one embodiment of the present invention. It is to be understood that this implant is but one of many embodiment implants in accordance with the present invention. Indeed, the present invention may have applicability to use in filling holes of various types of tissue, not just bone tissue.

Bone implant 400 includes a first portion 100 comprising a foam layer 110 and a sealant layer 120 (FIG. 5). As will be described further below, after implantation, bone implant 400 can be oriented within, for instance, a hole in the sella turcica 3 such that first portion 100 is disposed distally relative to second portion 200. Thus, first portion 100 primarily interacts with the dura matter 2, but also with the floor 33 of the sella turcica 3 and the surrounding soft tissue (see e.g., FIG. 6). Bone implant 400 also has a second portion 200 similarly comprising a foam layer 210 and a sealant layer 220. Second portion 200 primarily interacts with the mucosal membrane 8, but also with the floor 33 of the sella turcica 3 and the surrounding soft tissue (see e.g., FIG. 6). In addition, bone implant 400 has an intermediate foam layer 150 disposed between the first and second portions 100, 200. Intermediate foam layer 150 interacts with the dura matter 2, the floor 33 of the sella turcica 3 and the surrounding soft tissue (see e.g., FIG. 6).

In this particular embodiment, first and second portions 100, 200 are substantially symmetrical about the intermediate foam layer 150. Moreover, foam layers 110, 210 and intermediate foam layer 150 are all made of self-expanding foam. This self-expansion helps provide initial tightness and sealing between bone implant 400 and the hole before bone ingrowth occurs. Self-expanding foam is also desirable because it is good for filling an irregular shaped hole in a bone. As shown in the drawings, first and second portions 100, 200 are largely cylindrical. However, in other embodiments, the portions can be any shape suitable for providing the necessary seal between the implant and the hole Additionally, foam layers 110, 210 and intermediate foam layer 150 are all made of open cell foam that is resorbable. This is desirable because open cell foam is good for bone ingrowth where the bone implant 400 interfaces with the dura matter 2, the sella turcica 3, and the mucosal membrane 8 (see e.g., FIG. 6). Specifically, open cell foam that is resorbable may preferably be used for foam layers 150, 210 which interact with the mucosal membrane 8. Thus, bone implant 400 may be used to promote bone ingrowth in three key areas for durable and safe fixation; there may be ingrowth from the dura matter 62, ingrowth from the sella turcica 63, and ingrowth from the mucosal membrane 68 (FIG. 6). Additionally, the resorbable nature of the foam layers means that the implant does not need to be removed from the body, but rather, will ultimately be resorbed. It is to be understood that other implants in accordance with the present invention may include surfaces that facilitate different types of tissue ingrowth.

Open cell foam is also relatively elastic and works well with adhesives. For example, as shown in FIG. 5, intermediate foam layer 150 has a first surface 151 contacting the first portion 100 and a second surface 152 contacting the second portion 200. Surfaces 151, 152 further comprise an adhesive coating, such as fibrin-based glue, for improved adhesion between intermediate layer 150 and first and second portions 100, 200 respectively. It would also be possible for a surface 121 of the first portion 100 to include an adhesive coating for improved adhesion between sealing layer 120 and foam layer 110. It would similarly be possible for a surface 221 of second portion 200 to include an adhesive coating for improved adhesion between sealing layer 220 and foam layer 210. As a result, it is possible to use one or more adhesive coatings to form a rigid and tight closure of the hole 300. In turn, this may help prevent CSF leakage into the sphenoid sinus and the nasal cavity.

Sealant layers 120, 220 are made of an elastic material that is capable of forming a watertight barrier. Sealant layers 120, 220 also have a smaller thickness than foam layers 110, 210, wherein thickness is defined as a distance in the proximal to distal direction. Due to the material of sealant layers 120, 220, there is minimal biological interaction between the sealant layers 120, 220 and the surrounding anatomy (see e.g., FIG. 6).

Notably, sealant layer 120 of the first portion 100 extends radially outward beyond foam layer 110 of the first portion 100; whereas sealant layer 210 and foam layer 210 of the second portion 200 are of the same radial dimensions. In some applications, it may be desirable for the sealant layer 110 to extend beyond the foam layer 110 to create a better seal between bone implant 400 and the hole. For example, sealant layer 120 will have more surface contact with dura matter 2, as compared to the amount of surface contact between sealant layer 220 and mucosal membrane 8. This may be desirable to help prevent CSF leakage into the sphenoid sinus and the nasal cavity. Although described above as being constructed of a plurality of layers, implants according to the present invention could be constructed of a single layer. Thus, the implant could be entirely open or closed cell foam.

Figure 7:
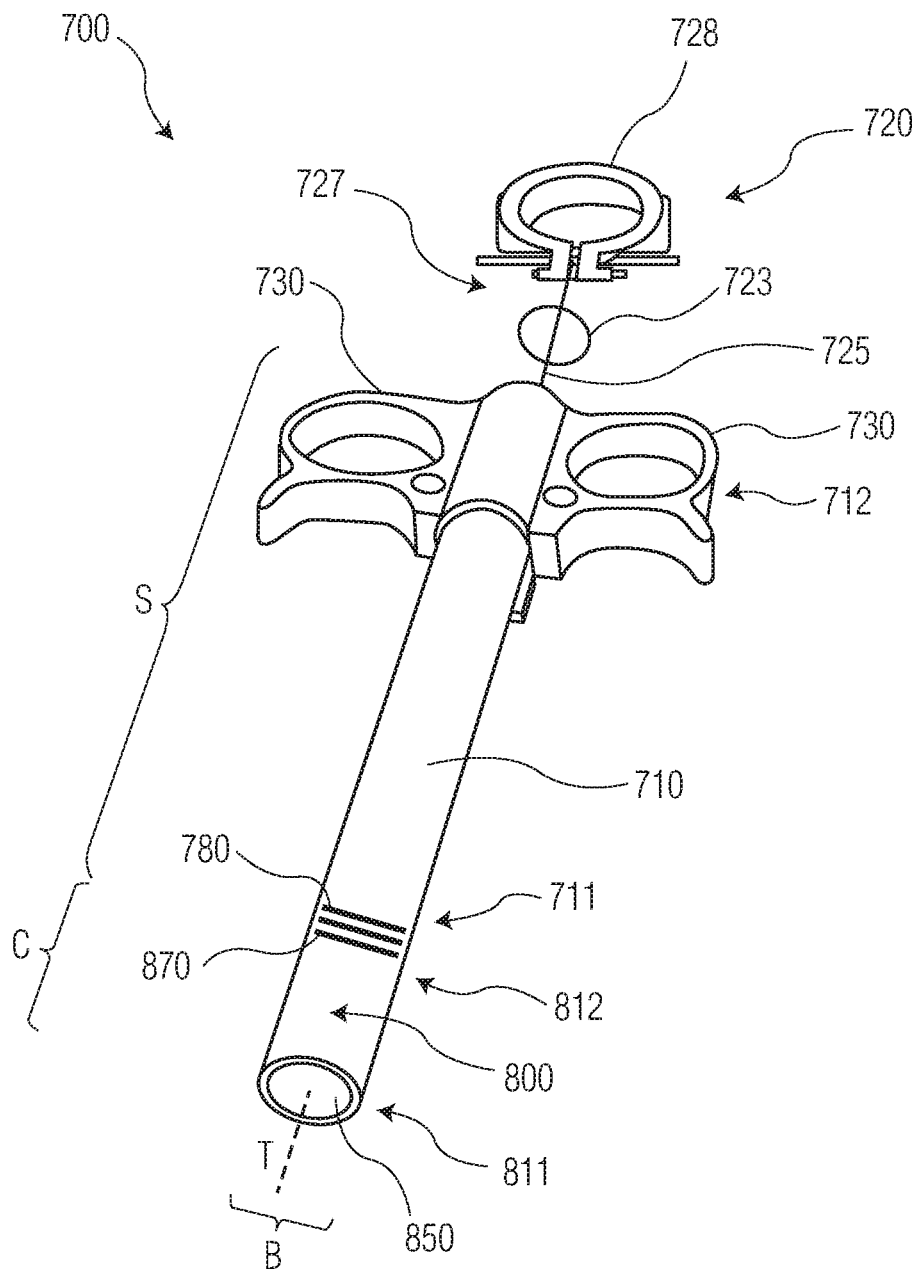
FIG. 7 is a perspective view of a delivery tool with a plunger.

Referring to FIG. 7, there is shown a delivery tool 700 in accordance with one embodiment of the present invention. Delivery tool 700 has a hollow shaft 710 with a distal end 711 and a proximal end 712 spaced apart along a tool axis T. Distal end 711 is adapted to engage with a proximal end 812 of cartridge 800. Accordingly, distal end 711 of shaft 710 includes attachment features 780 adapted to engage with complementary attachment features 870 on proximal end 812 of cartridge 800. As shown in FIG. 7, attachment features 780, 870 have complementary threading in this particular embodiment.

Delivery tool 700 also has a plunger 720 disposed within shaft 710 adapted to deploy the bone implant 400 from cartridge 800. Plunger 720 includes finger grips 730 extending radially outward from shaft 710 near its proximal end 712. Plunger 720 also includes handle 728 which may be in the form of a thumb ring disposed near the proximal end 712 of shaft 710.

Handle 728 is attached to a rod 725 extending through shaft 710. Rod 725 has a distal end 726 (not shown) and a proximal end 727 spaced apart along tool axis T. Rod 725 also includes a reference marker 723 to indicate the location of distal end 726 of rod 725 within shaft 710, as will be explained below.

Cartridge 800 has distal and proximal ends 811, 812 extending along tool axis T and a bore 850 extending therebetween. Bore 850 is sized to receive bone implant 400 in its fully compressed position, as will be described further below. Bore 850 is also sized to receive rod 725. For example, in the preferred embodiment, bore 850 has a diameter B of approximately 4-8 mm. Also, proximal end 812 of cartridge 800 includes attachment features 870 engageable with complementary attachment features 780 on shaft 710, as discussed above. These attachment features 780, 870 are desirable because translation of rod 725 within bore 850 should not disengage cartridge 800 from delivery tool 700.

The embodiment of delivery tool 700 of FIG. 7 has a relatively long shaft length S for clarity of illustration, wherein shaft length S is defined as a distance between distal and proximal ends 711, 712 along tool axis T. In reality, there may be a short shaft length S, wherein a portion of the shaft 710 is made of a flexible material so that shaft 710 may navigate the entire trajectory through the patient's anatomy and to the sella region near the pituitary gland 1. Similarly, a portion of rod 725 may also be made of a flexible material for ease of implantation.

Additionally, delivery tool 700 has a relatively short cartridge length C for clarity of illustration, wherein cartridge length C is defined as a distance between distal and proximal ends 811, 812 along tool axis T. In reality, there may be a long cartridge length C so that the cartridge 800 may navigate the entire trajectory through the patient's anatomy and to the sella region near the pituitary gland 1.

In operation, as will be described further below, delivery tool 700 may be used to dispose bone implant 400 within a hole in the sella turcica 3. However, before implantation, many surgeons may wish to conduct preoperative planning in order to reduce the risk of injury to the patient. This is an optional step that need not be conducted in every surgery. However, some level of preoperative planning may further aid the surgeon in conducting a successful surgery.

Figure 1:
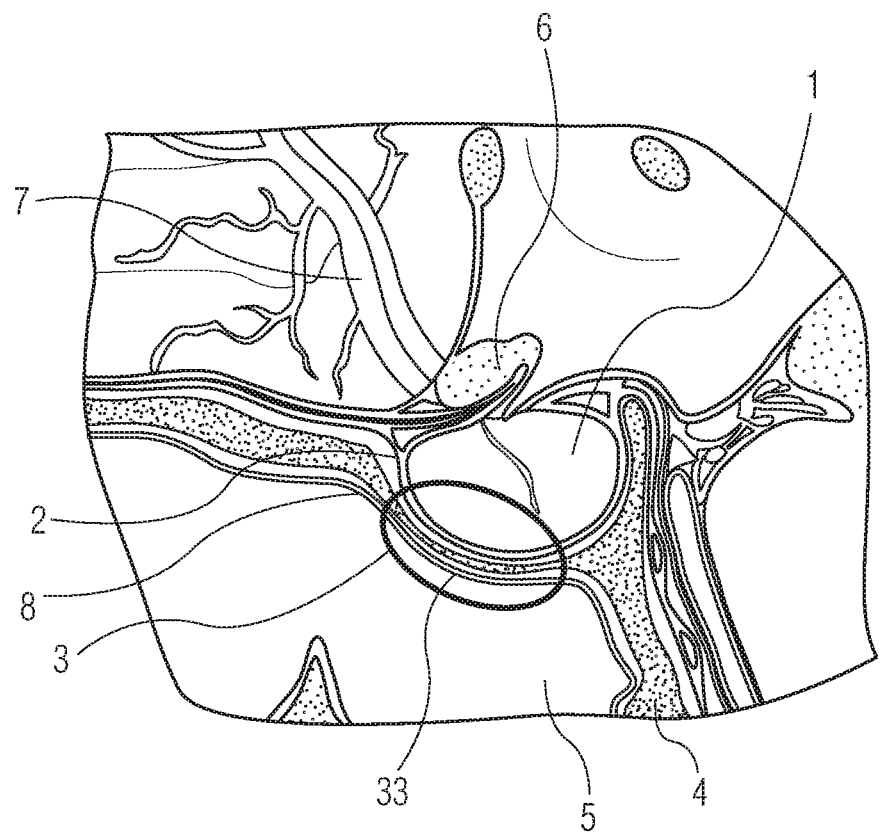
FIG. 1 is an anatomical cross-sectional view of a pituitary gland.
Figure 2:
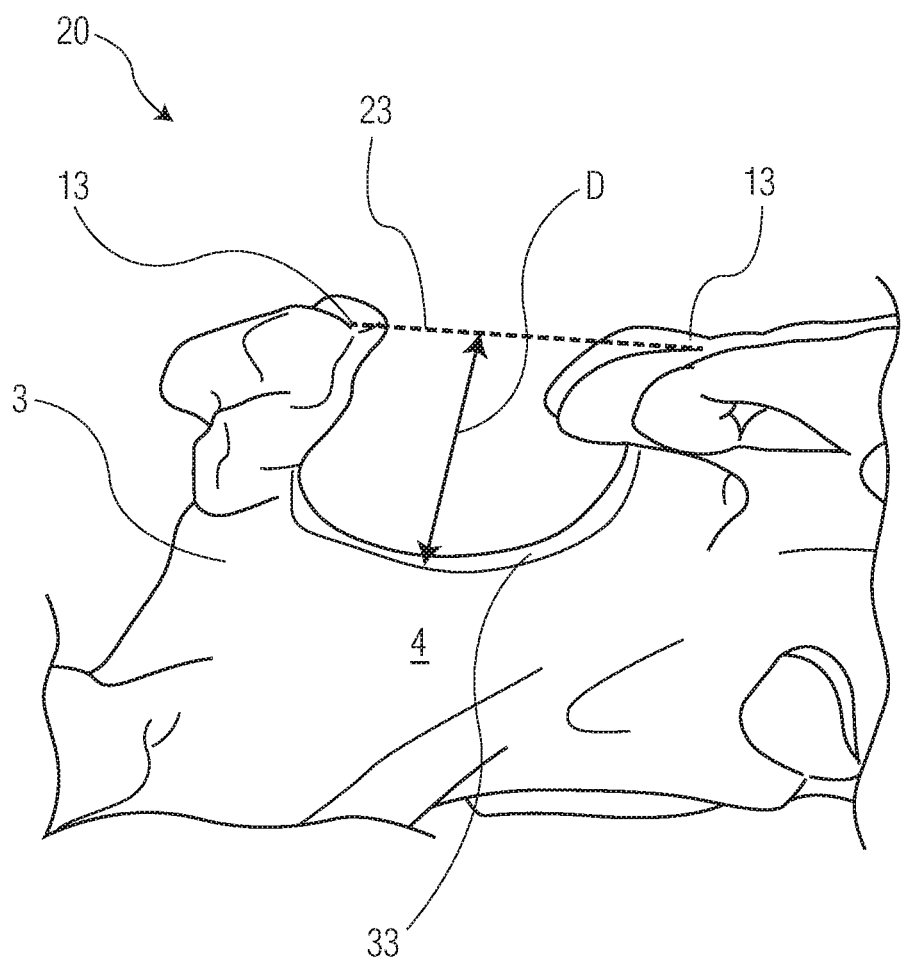
FIG. 2 is a side view of a computer model of a sella turcica.
Figure 3:
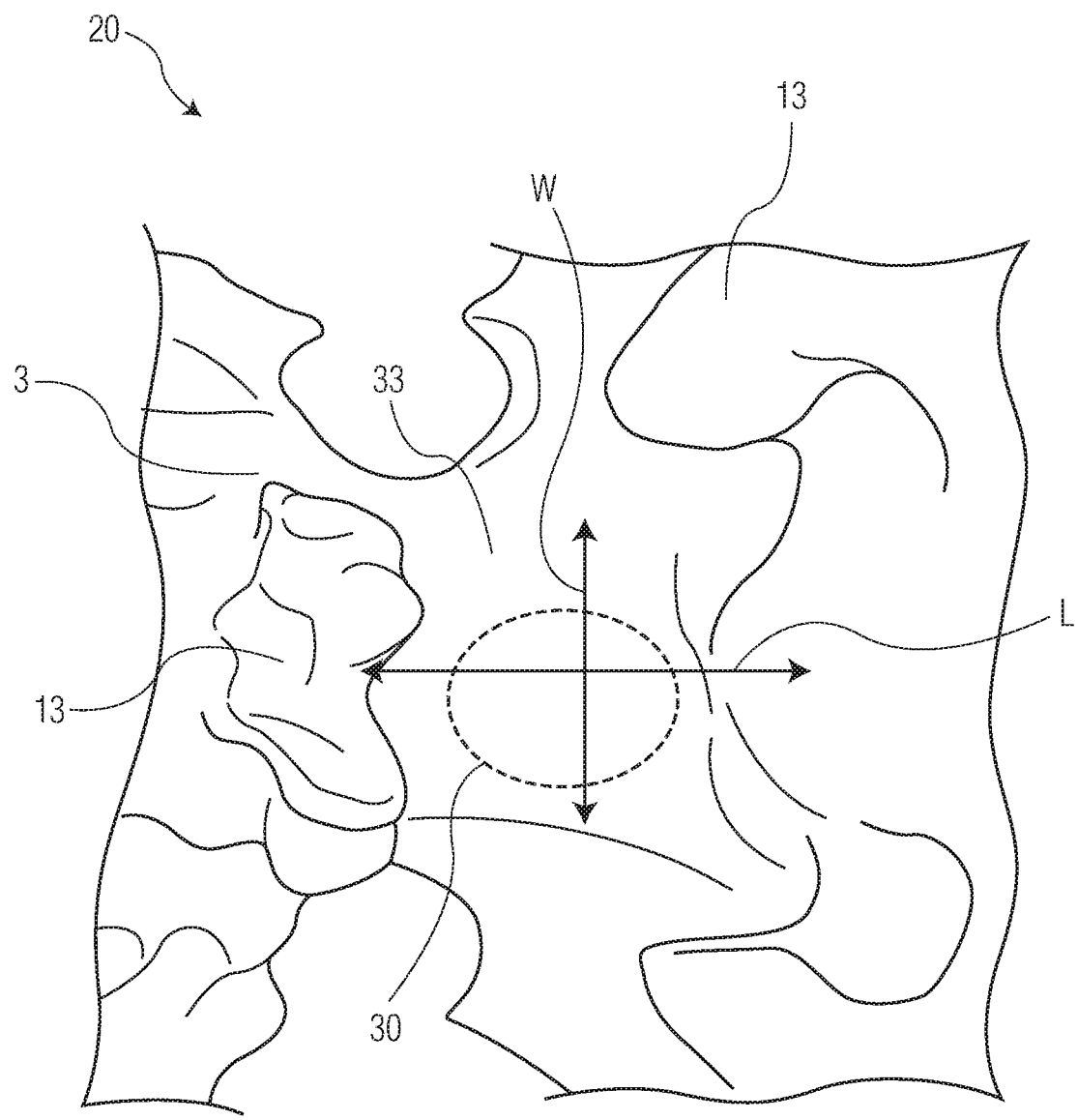
FIG. 3 is a top view of the computer model of the sella turcica of FIG. 2.

In some applications, the surgeon may use a software application to analyze 3D scan slices to create a 3D bone model 20 of sphenoid bone 4. As shown in FIG. 2, it may be desirable to calculate a depth D of the clinoid processes of the sella turcica 3. For example, the depth D may be approximately 1-11 mm. To make the calculation, the software application may be used to define an axis 23 between distal apices 13 of the sella turcica 3. Then, the depth D is defined as a distance between axis 23 and a floor 33 of the sella turcica 3. As shown in FIG. 3, it may also be desirable to calculate a length L and a width W of the sella turcica 3 at various depths D. For example, the length L may be approximately 5-16 mm and the width W may be approximately 1-24 mm at various depths D. To make the calculation, the software application may define length L as a distance along axis 23 between distal apices 13 of the sella turcica 3 and a width W may be defined as a distance perpendicular to axis 23. Accordingly, it is possible for the surgeon to adjust axis 23, depth D, length L, and width W for real-time calculations using the 3D bone model 20. Thus, the surgeon is able to better visualize the sellar region near the pituitary gland 1 in 3D. Nonetheless, implants in accordance with the present invention may be offered in different sizes and/or shapes. Moreover, the selected implant may be based upon imaging results prior to or during the surgery.

Next, the surgeon can preoperatively plan a profile 30 that represents the hole to be created in the floor 33 of the sella turcica 3 based on the patient's specific anatomy. Although the profile 30 shown herein is substantially ovular, in many applications, the profile and the resulting hole will be irregular in shape. This often contributes to the duration and difficulty of the transsphenoidal procedure. As a result, it is desirable for the surgeon to be able to preoperatively plan and visualize the trajectory of an instrument through the patient's anatomy and through the profile 30 of the hole, to simulate accessing the sellar region near pituitary gland 1. If desired, the surgeon may adjust the visualized trajectory so that it is relatively minimally invasive based on the 3D bone model 20.

Using the 3D bone model 20, the surgeon is also able to then, for example, preoperatively plan the size for a fat graft after removal of a tumor in the sellar region near the pituitary gland 1. Additionally, the surgeon is able to preoperatively plan the appropriate size, shape and material of bone implant 400 that will be used to seal the hole created in the floor 33 of the sella turcica 3. For example, the surgeon may select the desired size and foam material of first and second portions 100, 200 and intermediate foam layer 150. Further still, the surgeon is able to preoperatively plan and design the appropriate size and material of delivery tool 700 for disposing bone implant 400 within hole 300. Desirably, a surgeon may calculate the appropriate shaft length S and cartridge length L for different embodiments of delivery tool 700 based on the visualized trajectory during preoperative planning, as previously discussed. A surgeon may also choose to use a disposable or a reusable cartridge during preoperative planning.

Once the surgeon has completed preoperative planning using 3D bone model 20, the surgeon may insert a cutting tool (not shown) into the patient and advance the cutting tool along the preoperatively planned travel path through the patient's anatomy and to the sellar region near the pituitary gland 1. Then, the cutting tool may be used to form the hole in the floor 33 of the sella turcica 3 according to the preoperatively planned profile 30 of the 3D bone model 20. After, the cutting tool can be removed from the patient and the tumor near the pituitary gland 1 can be removed. Optionally, a fat graft (not shown) can be used to fill the empty space where the tumor once was.

Next, the surgeon may obtain the desired bone implant 400 and delivery tool 700 which are both of appropriate size and material based on the patient's specific anatomy. Then, the first and second portions 100, 200 of bone implant 400 may be placed in the first and second compressed positions respectively. In the fully compressed position, bone implant 400 may fit within bore 850 of the cartridge 800 (FIGS. 4 and 9).

FIG. 4 shows bone implant 4 in the fully compressed position, when first and second portions 100, 200 are in there first and second compressed positions respectively. Additionally, first portion 100 should be positioned near the distal end 811 of cartridge 800, while the second portion 200 should be positioned near the proximal end 812 of cartridge 800.

The proximal end 812 of cartridge 800 may optionally be threaded onto the distal end 711 of shaft 710 before or after loading bone implant 400 into cartridge 800. Therefore, the distal end 726 of rod 725 abuts the second portion 200 of bone implant 400. At this point, delivery tool 700 with bone implant 400 loaded therein may be inserted into the patient and advanced along the preoperatively planned travel path through the patient's anatomy and to the sellar region near the pituitary gland 1.

Figure 9:
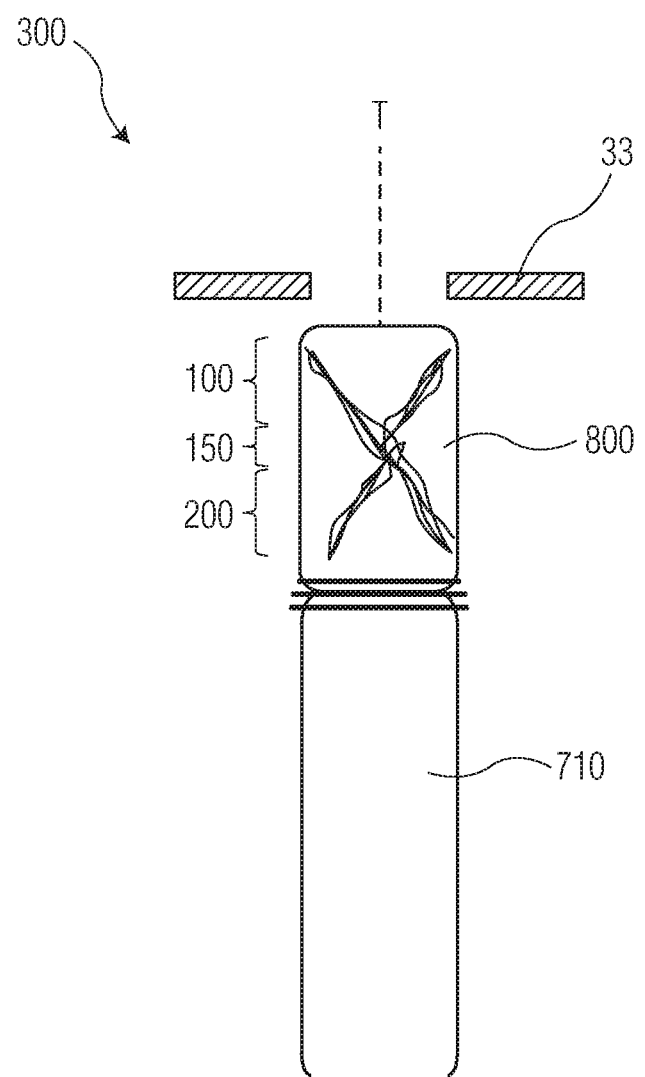
FIGS. 9-11 schematically illustrate a method of using an implant and a delivery tool with a plunger.

As shown in FIG. 9, distal end 811 of cartridge 800 approaches the hole 300 in the floor 33 of the sella turcica such that distal end 811 and hole 300 may be coaxially aligned with respect to tool axis T. The distal end 811 of cartridge 800 may ultimately abut the floor 33 of the sella turcica 3.

Figure 8:
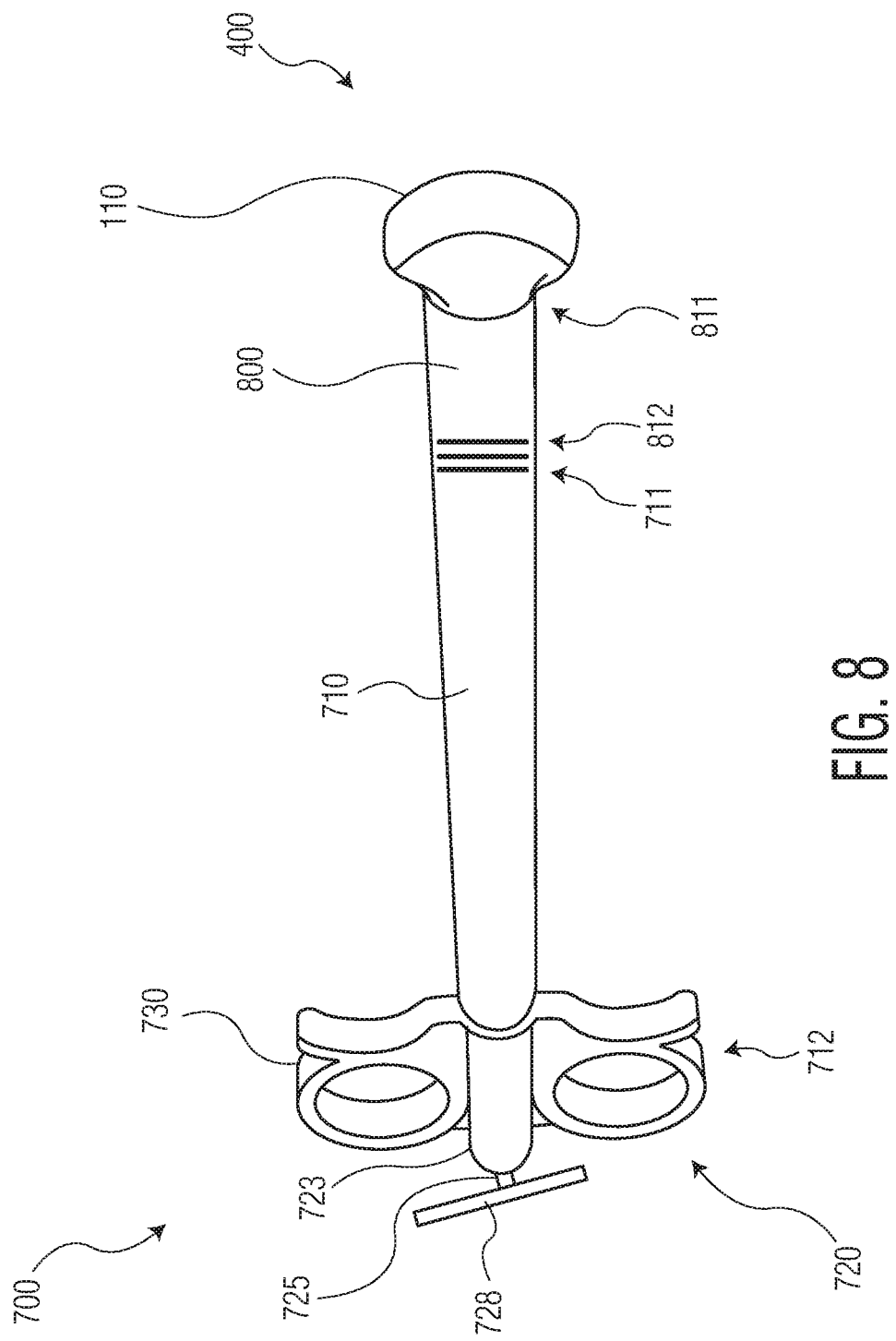
FIG. 8 is another perspective view of the delivery tool of FIG. 7 with the plunger at a first stop position.
Figure 10:
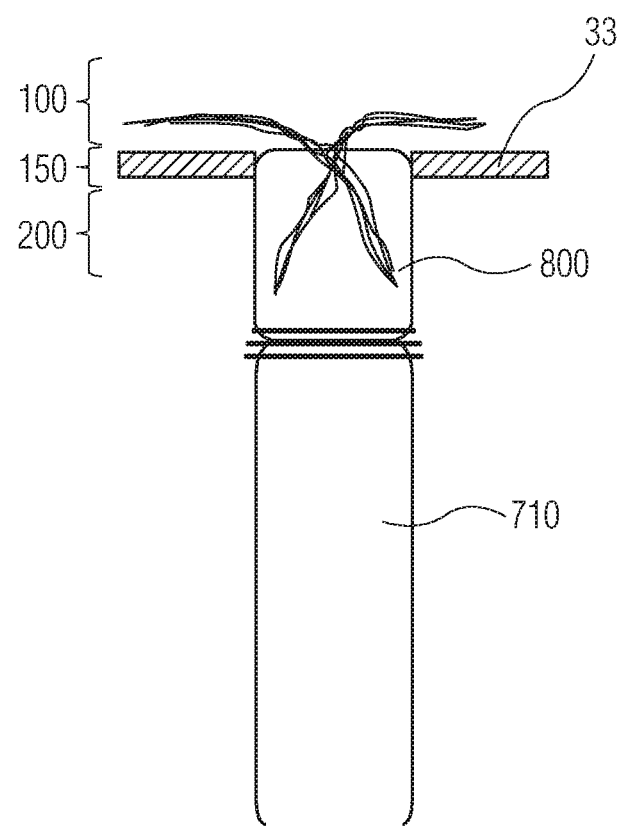

When a force is applied to handle 728, while holding finger grips 730, rod 725 advances in the distal direction along the tool axis T relative to shaft 710. That is, the distal end 726 of rod 725 may advance a first preoperatively planned distance within shaft 710 and also a first preoperatively planned distance within bore 850. Rod 725 may continue to advance until the reference marker 723 abuts the proximal end 712 of shaft 710. This indicates that plunger 720 has reached a first stop position (FIGS. 8 and 10). At the same time, rod 725 forces bone implant 400 in a distal direction relative to cartridge 800 such that the first portion 100 of bone implant 400 is forcibly inserted through hole 300 in its first compressed position and thereby, released from cartridge 800.

Upon release, first portion 100 is allowed to self-expand to transition from its first compressed position to its first deployed position. As shown, this self-expansion occurs in a radially manner, however, the portion could be designed to expand from a fold, bend or the like. Said another way, the thickness of first portion 100 decreases as it transitions from its first compressed position to its first deployed position. First portion 100 cannot pass through hole 300 when in the first deployed position without deformation. At this point, bone implant 400 is considered partially deployed (FIGS. 8 and 10). Still, second portion 200 remains in its second compressed position within the cartridge 800.

The surgeon may apply some force in the proximal direction to try to pull first portion 100 relative to hole 300 in order to ensure that first portion 100 cannot pass through hole 300 in the first deployed position without deformation. If first portion 100 does pull through hole 300, it may be necessary to perform manipulation utilizing additional instruments (not shown) or it may be required to place a differently sized implant.

Figure 11:
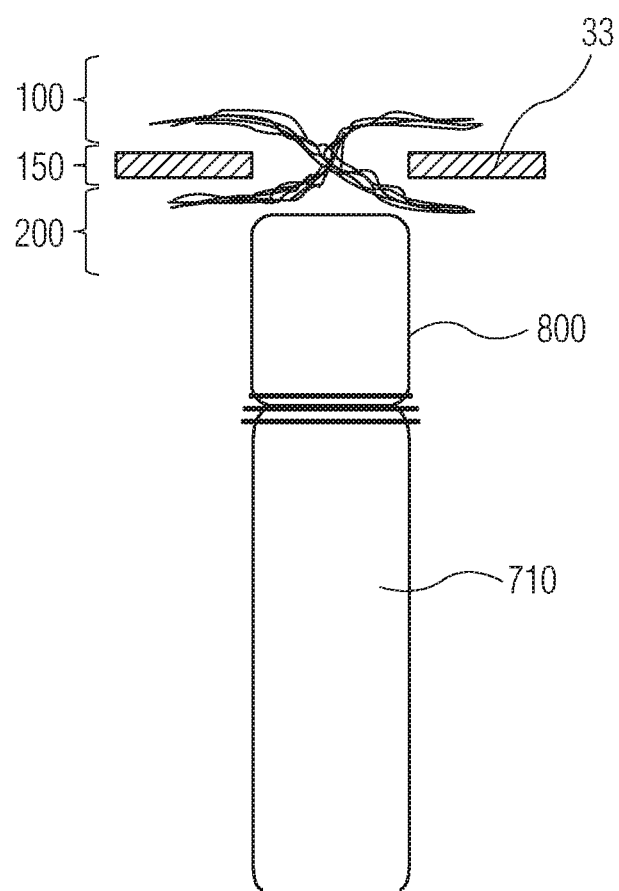

Then, additional force can be applied to handle 728 to further advance rod 725 in the distal direction relative to shaft 710. That is, distal end 726 of rod 726 has advanced a second preoperatively distance within shaft 710 and a second preoperatively planned distance within bore 850. Rod 725 may continue to advance in the distal direction, thereby causing reference marker 723 to slide along rod 725 in a proximal direction, until the marker abuts both proximal end 712 of shaft 710 as well as handle 728. This indicates that plunger 720 has reached a second stop position and rod 725 cannot continue to advance in the distal direction (FIG. 11). At the same time, rod 725 forces bone implant 400 in a distal direction relative to cartridge 800 such that the second portion 200 of bone implant 400 is forcibly released from the cartridge 800. Upon release, second portion 200 is allowed to radially self-expand to transition from its second compressed position to its second deployed position (FIGS. 5-6 and 11).

At this point, bone implant 400 is considered fully deployed. Both first and second portions 100, 200 have radially self-expanded such that neither portion 100, 200 is able to pass through hole 300. Said another way, the thicknesses of the first and second portions 100, 200 prevents their passing through the hole without contraction or a decrease in their overall footprint. This may provide a rigid and tight closure of the hole 300 and may help prevent CSF leakage. It may also help encourage bone ingrowth into bone implant 400 for durable and safe fixation.

Once bone implant 400 is properly disposed within hole 300, the delivery tool 700 may be removed from the patient and cartridge 800 may be discarded. After, bone implant 400 may show good bone growth within a relatively short amount of time in situ, e.g., three weeks. Bone implant 400 may also be at least somewhat naturally resorbed by the body after a desired amount of time in situ, e.g., six to eight weeks, due to the nature of the open cell resorbable foam in layers 100, 200, and 150.

Different features of different embodiments of bone implant 400 and delivery tool 700 may be desirable for different transsphenoidal and/or orthopedic applications. For instance, regarding bone implant 400, different embodiments of first and second portions 100, 200 of bone implant 400 may not be substantially symmetrical; they may have different thicknesses or different radial dimensions. Different embodiments may also include different foam layers 110, 210 and sealing layers 120, 220. There also may be no sealing layers 120, 220 in first and second portions 100, 200.

Different embodiments of first and second portions 100, 200 and intermediate foam layer 150 may not use the same open cell resorbable foam as described earlier. For example, rather than using an open cell foam that is resorbable, it is possible to use an open cell foam that is not resorbable. Comparatively, open cell foam that is not resorbable has more rigidity and stiffness. Open call foam that is not resorbable is also highly elastic and may provide a potential shape memory effect if desired. Specifically, open cell foam that is not resorbable may preferably be used for intermediate foam layer 150 which interacts with the sella turcica 3.

Alternatively, it would be possible to use a closed cell foam in the first and second portions 100, 200 and intermediate foam layer 150. Closed cell foam may exhibit less bone ingrowth as compared to open cell foam. However, closed cell foam can be compressible through pressure from surrounding tissue, such as dura matter 2. Specifically, closed cell foam may preferably be used for foam layers 150, 110 which interact with the dura matter 2.

It is also possible for bone implant 400 to be made of a biodegradable material. All materials used for bone implant 400 should nonetheless be sterilizable and biocompatible.

Different embodiments of first and second portions 100, 200 and intermediate foam layer 150 could be made of an inflatable material, rather than a self-expanding material. Those embodiments would likely require some actuator, e.g., a fluid line that is insertable through the shaft 710 of the delivery tool 700 and through the bore 850 of the cartridge 800. In such embodiments, it may not even be necessary to load the bone implant into a cartridge before implantation.

During implantation, this actuator could be used to cause the first and second portions to transition from the first and second compressed positions to the first and second deployed positions respectively. Still, it could be possible to independently deploy the first and second portions in these embodiments.

Depending on the embodiment of bone implant 400, there may be sufficient bone ingrowth and/or scar formation to remove the bone implant after only a few weeks from delivery, rather than leaving bone implant 400 in situ for a long period of time. This could be done utilizing standard instruments, but caution must be given not to damage the dura and cause further CSF leaks. Or, as mentioned earlier, it is possible for a bone implant to be made of a biodegradable material such that it is naturally removed.

Different embodiments of delivery tool 700 may be designed to safely deliver the desired embodiment of bone implant 400. There may also be varied features of different embodiments of delivery tool 700 to appeal to physician preference, for example, the design of the handle or of the plunger. For example, in some embodiments, the handle may be a flat circular top that can be pressed like a syringe, rather than a thumb ring. As another example, there may be finger grips that partially or fully encircle the finger. There may alternatively be a sleeve securably disposed around a portion of the shaft such that the sleeve could be held and used as a means for finger grips. The plunger itself could also be actuated using an automated system rather than manual force.

The physician may choose the appropriate size and material of the shaft and of the cartridge during preoperative planning, based on the specific patient's anatomy. For example, the shaft and rod may need to be longer and more flexible if the anatomy is more tortuous. The shaft and the cartridge may also need to be radially smaller. All of these factors may affect the preoperatively planned distances the rod will travel within the shaft and the bore at the first and second stop positions, respectively.

In some embodiments, the bone implant may come preloaded in the cartridge. In some other embodiments, the cartridge may also be formed as an integral part of the shaft rather than as a separate element.

Overall, the devices and methods according to the present disclosure can provide several advantages for different transsphenoidal applications that require a bone implant to fill a hole in a bone, such as in other frontal skull base regions that are in communication with the sinus passages or the like. The same devices and methods may also be applied to other orthopedic applications using bone implants to fill a hole in a bone. For instance, the devices and methodology of the present disclosure may be used to fill a hole in the ethmoid and sphenoid bones.

Thus, it is possible to use 3D bone model 20, bone implant 400, and/or delivery tool 700 for simple, fast, and effective ways to fill the hole in the sella turcica. The available preoperative planning can help reduce the duration and difficulty of the procedure. The design of bone implant 400 is also easy to use with delivery tool 700 and only requires two steps for disposal within the hole in the sella turcica: partial deployment and full deployment.

When fully deployed, bone implant 400 is desirable for filling a hole in the sella turcica that has an irregular shape. The self-expanding foam of bone implant 400 creates a tight seal and grows to fit the irregular shape of the hole upon deployment. The open cell foam material further promotes bone ingrowth for safe and durable fixation of bone implant 400. The open cell foam material is also resorbable such that bone implant 400 may be left in situ for long periods of time. Many of these factors help create and maintain a tight seal of the hole is in order to reduce CSF leakage into the sphenoid sinus and the nasal cavity.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant configured to close a hole in bone tissue comprising:
   a first portion having a first compressed position and a first deployed position, the first portion having a first diameter in the first deployed position, the first portion including a first sealant layer;
   a second portion having a second compressed position and a second deployed position, the second portion having a second diameter in the second deployed position, the second portion including a second sealant layer;
   an intermediate portion between the first sealant layer and the second sealant layer, the intermediate portion having a third diameter smaller than the first diameter and the second diameter, and
   wherein the first and second portions can be deployed independently.

2. The implant of claim 1, wherein the intermediate foam layer to promote bone ingrowth is disposed between the first and second portions.

3. The implant of claim 2, wherein the intermediate foam layer comprises an open cell foam.

4. The implant of claim 2, wherein the intermediate foam layer and the first and second portions are at least partially resorbable.

5. The implant of claim 2, wherein the intermediate foam layer has first and second surfaces contacting the first and second portions respectively, wherein the surfaces include an adhesive coating.

6. The implant of claim 5, wherein the first and second portions further comprise an adhesive coating on at least one surface.

7. The implant of claim 1, wherein the first sealant layer creates a watertight barrier and a first foam layer to promote bone ingrowth.

8. The implant of claim 7, wherein the first foam layer comprises an open cell foam.

9. The implant of claim 1, wherein the second sealant layer creates a watertight barrier and a second foam layer to promote tissue ingrowth.

10. The implant of claim 9, wherein the second foam layer comprises an open cell foam.

11. The implant of claim 1, wherein the first and second portions are self-expanding upon deployment in order to transition from their compressed positions to their deployed positions.

12. The implant of claim 1, wherein the first and second portions can be inflated to transition from their compressed positions to their deployed positions.

13. The implant of claim 1, wherein the first and second portions are made of a biodegradable material.

14. The implant of claim 1, wherein the first and second portions fit within a bore in a cartridge when in their compressed positions.

15. The implant of claim 1, wherein the first portion is configured to contact an inner surface of the bone tissue that surrounds the hole when in the first deployed position.

16. The implant of claim 1, wherein the second portion is configured to contact an outer surface of the bone tissue that surrounds the hole when in the second deployed position.

17. The implant of claim 1, wherein the intermediate portion has a first and second end, wherein the first sealant layer is a distance away from the first end of the intermediate portion and the second sealant layer abuts the second end of the intermediate portion.

18. The implant of claim 1, wherein the first sealant layer has a first sealant diameter and the second sealant layer has a second sealant diameter, the first sealant diameter being greater than the second sealant diameter.

* * * * *